United States Patent [19]

Schammel et al.

[11] Patent Number: 4,845,275
[45] Date of Patent: Jul. 4, 1989

[54] TRIMELLITIC ACID PROCESS

[75] Inventors: Wayne P. Schammel, Naperville; Michael R. Green, Geneva, both of Ill.

[73] Assignee: Amoco Corporation, Chicago, Ill.

[21] Appl. No.: 249,591

[22] Filed: Sep. 26, 1988

[51] Int. Cl.$^4$ .............................................. C07C 51/215
[52] U.S. Cl. ..................................... 562/416; 502/227; 562/417
[58] Field of Search ................................ 562/416, 417

[56] References Cited

U.S. PATENT DOCUMENTS 4,230,882 10/1980 Seko et al. ............................ 562/416
4,314,073  2/1982 Crooks .................................. 562/416
4,322,549  3/1982 Kuhlmann et al. .................. 562/416

Primary Examiner—Werren B. Lone
Assistant Examiner—Vera C. Clarke
Attorney, Agent, or Firm—Gunar J. Blumberg; William H. Magidson; Ralph C. Medhurst

[57] ABSTRACT

An improved process for the manufacture of trimellitic acid from pseudocumene feedstock is disclosed. In this process, lead (IV) is used as a catalyst component in addition to the cobalt, manganese, and zirconium catalyst. The use of lead (IV) reduces higher boiling impurities and improves the yield. In our novel process, pseudocumene is converted to trimellitic acid which is used to manufacture plasticizers and polyamide-imide polymers used as molding compounds for replacement of metals.

6 Claims, No Drawings

TRIMELLITIC ACID PROCESS

The addition of lead (IV) to oxidation catalysis provided by a heavy, transition metal-bromine ion combination containing at least a manganese ion uniquely increases catalytic selectivity of said combination for converting methyl groups to carboxylic acid groups on the aromatic nucleus of pseudocumene (PSC). Such greater catalytic selectivity is manifested by lower high molecular weight by-product formation, improved yield and improved color.

Our novel process relates to the liquid phase oxidation of PSC using cobalt, manganese and/or other varia- ble-valence metals plus bromine with or without zirconium and about 1000 to about 8000 parts per million of lead (IV), based on the PSC feedstock. Our novel invention is a process for the oxidation of PSC, with molecular oxygen to trimellitic acid (TMLA) under liquid phase conditions utilizing a zirconium-cobalt-magnesium-bromine catalyst, in the presence of about 1000 to about 8000 parts per million of lead (IV), based on the PSC feedstock, preferably 3000 to 6000 parts per million of lead (IV), and wherein the atomic ratio of zirconium to cobalt is in a range from about 1 to about 10 to about 1 to about 100, which process comprises conducting a batch oxidation of the PSC at a temperature of about 100° C. to about 275° C., preferably at a temperature of about 120° C. to about 225° C. The solvents in our reaction are lower aliphatic acids having about $C_2$ to $C_5$ hydrocarbons, however, the preferred aliphatic acid is acetic acid.

The prior art has not recognized the use of lead (IV) as a catalytic component in the manufacture of TMLA using PSC as feedstock. Lead has been used in certain other oxidations as disclosed in the following Czechoslovakian certificates of authorship; 190,160, 200,136 and 222,750. It should be noted that in our process only lead (IV) is useful; lead (II) does not increase the yield of TMLA.

While it is known in the art that heavy metals in combination with bromine can be used to catalyze the oxidation of polyalkylaromatics to their corresponding polycarboxylic aromatic acids as taught in U.S. Pat. No. 2,833,816; it has not previously been shown that our invention of adding lead (IV) to the heavy transition metal-bromine ion catalyzed oxidation of PSC will increase the selectivity of the catalyzed oxidation reaction whereby TMLA is produced in high yield, with fewer impurities and with superior color.

Our invention also includes a process for the oxidation of PSC with molecular oxygen to TMLA under liquid phase conditions in the presence of a manganese-bromine or cobalt-manganese-bromine catalyst and in the presence of about 1000 to about 8000 parts per million of lead (IV), based on the PSC feedstock, at a temperature of about 100° C. to about 275° C.

We have found that adding lead (IV) salts to the catalyst mix enhances the selectivity of the oxidation of PSC to TMLA. Specifically, we have seen dramatic reductions (>50%) in high boiling impurities without any large losses in activity. Our novel process has a significant impact on the yield in the reaction as well as a substantial improvement in color quality.

It has always been advantageous to improve the selectivity and yield during PSC oxidations since this improves the efficiency of the operation and has considerable value in practice. An example of a prior improvement is bromine staging which increased the yield of TMLA by 1.8 mole %.

TMLA product quality has to be improved and we have solved this problem by preventing the formation of some of the by-products in the reaction portion of the process. It is well established that high boiling impurities which are formed during the oxidation contain color bodies some of which eventually make it to the TMLA product.

In our novel process, high boiling impurities are reduced and both the selectivity and color quality of TMLA are significantly improved.

The yield of PSC oxidations are in the range of about 89.8 to 90.5 mole % by adding about 1000 to 8000 parts per million based on PSC of lead (IV). Particularly, the yield increase was attributed to the large reduction in the high boilers. This reduction was in the range of 50–60%. Because of this process improvement, the color of the reactor effluent was visibly lighter.

To achieve this improvement, lead (IV) was added at a level of about 0.10 to 0.80 wt % based on PSC. In our novel process, lead (IV) modulates the catalytic activity in the early phase of the reaction thus precluding the formation of high boiling impurities.

Zirconium and lead (IV) can be added to the reaction in any form soluble in the PSC being oxidized or in acetic acid when it is being used as reaction solvent. For example, zirconium octanoate or naphthenate can be used with manganese and cobalt octanoates or naphthenates for oxidation of PSC in the absence of reaction solvent, and each of Zr, Mn, and Co can be conveniently used as its acetate when PSC is oxidized in the presence of acetic acid solvent. Suitably, lead (IV) is added in the form of lead acetate, lead oxide, lead chloride. Zirconium is available on a commercial basis as a solution of $ZrO_2$ in acetic acid and, as such, is ideally suited for liquid phase oxidations using acetic acid as reaction solvent. However, there is no limitation in which form the lead (IV) or zirconium is added, provided, it is soluble or becomes soluble in the reaction medium.

The source of molecular oxygen for the enhanced oxidation of this invention can vary in $O_2$ content from that of air to oxygen gas. Air is the preferred source of molecular oxygen for oxidations conducted at temperatures of 100° C. and above, up to 275° C. For oxidations conducted with molecular oxygen, the preferred temperatures are in the range of about 120° C. to about 225° C. The minimum pressure for such oxidations is that pressure which will maintain a substantial liquid phase of 70–80% of the reaction medium, either neat PSC or PSC and 70–80% of the acetic acid. The acetic acid solvent, when used, can amount to 0.5–4.0 parts on a weight basis per part of the PSC. The PSC and/or acetic acid not in the liquid phase because of vaporization by heat of reaction is advantageously condensed and the condensate returned to the oxidation as a means for removing heat and thereby temperature controlling the exothermic oxidation reaction. Such vaporization of PSC reactant and/or acetic acid solvent is also accompanied by vaporization of lower boiling by-product water. When it is desired to take advantage of the benefits of withdrawing acetic acid and water of reaction from the liquid phase oxidation, as will be hereinafter demonstrated, condensate is not returned to the oxidation.

Batch reactions are successful because high concentrations of the product acid occur near the end of the oxidation while in continuous oxidations the product concentration is at a constant high level. Batch oxidations, however, have disadvantages because the concentration of the hydrocarbon near the beginning of the oxidation is high and its rate of oxidation is difficult to control. This leads to a low concentration of dissolved oxygen and increased amounts of hydrocarbon radical reactions producing dimeric, high-boiling side products which reduce the yield. These disadvantages have been overcome in our novel process by the addition of about 1000 to 8000 parts per million of lead (IV), based on the PSC feedstock.

Our process is a process for oxidizing PSC to TMLA which comprises catalytically oxidizing the PSC feedstock with air in the presence of an aliphatic acid in an oxidation zone wherein liquid phase conditions are maintained and wherein the weight ratio of aliphatic acid to the polyalkylaromatic is in the range of about 0.5–4.0:1.0 and the catalyst comprises one or more heavy metal oxidation catalysts and a source of bromine, the process comprises addition of a combination of sources of cobalt, manganese, zirconium and bromine components to provide about 0.05 to about 0.4 weight percent total metals based on the PSC feedstock and further adding about 1000 to about 8000 parts per million by weight of lead (IV) based on PSC in at least one stage wherein there is present a weight ratio of bromine ions to total metals ions of about 0.5–30:1.0, a zirconium content of about 1–10 percent and a manganese content of about 10–50 percent each by weight of the total metals, and the reaction is conducted at a temperature of about 100° C. to about 275° C.

In our novel batchwise oxidation of PSC, the exothermoic heat of reaction vaporizes some of the liquid solvent which is carried out of the reaction by the process air. The solvent is condensed and returned to the reactor as reflux. This liquid reflux is reheated toward the end of the reaction cycle to ensure temperatures high enough to bring the oxidation to completion. After reaction, the reactor contents are depressurized and TMLA is crystallized out to form a 50-60% solids slurry (close to the maximum solids concentration that is pumpable). The solids are filtered out and further processed into final product. The filtrate is disposed of and, therefore, represents a significant yield loss.

Another alternate and suitable mode of conduct for the catalytic liquid phase air oxidation of PSC to TMLA is staged addition of the bromine component. This improved mode of conduct provides reduced impurity levels, improved color and lower solvent and pseudocumene burning while improving the high yields of the desired acid. This improved staging of the bromine component permits the use of lower metals and acetic acid-to-PSC ratios, and provides a crude TMLA product of lower metals and bromine-containing impurities which can be more conveniently removed from crude TMLA. Other advantages from this improved mode of conduct for bromine staging will be apparent from the disclosure which follows.

Our process comprises a process for oxidizing PSC to TMLA which comprises catalytically oxidizing PSC feedstock with air in the presence of an aliphatic acid in an oxidation zone wherein liquid phase conditions are maintained and wherein the weight ratio of aliphatic acid to PSC is in the range of about 0.5–4.0:1.0 and the catalyst comprises one or more heavy metal oxidation catalysts and a source of bromine, the process comprises addition of a combination of sources of cobalt, manganese, zirconium and bromine components to provide about 0.05 to about 0.4 weight percent total metals based on PSC and further adding about 1000 to about 8000 parts per million by weight of lead (IV) based on PSC in at least one stage wherein there is present a weight ratio of bromine ions to total metals ions of about 0.5–3.0:1.0, a zirconium content of about 1–10 percent and a manganese content of about 10–50 percent each by weight of the total metals, and the reaction is conducted at a temperature of about 100° C. to about 275° C.

It is particularly desirable to oxidize PSC as completely as possible to TMLA not only to obtain high yields of that acid product in the oxidation effluent but also to provide potential of recovery of crude TMLA product with low partial oxidation impurities but also without extensive oxidation of acetic acid. Low impurity formation is a goal also desirable because TMLA is rather soluble in acetic acid and the methylphthalic acids' and formylphthalic acids' impurities appear to enhance the solubility of TMLA leading to contamination of the product precipitated from the oxidation effluent, especially a concentrate thereof. Thus, the partial oxidation products in the oxidation effluent have a limiting effect on TMLA precipitation by crystallization from said effluent, making necessary additional processing steps to effect recovery of the remaining TMLA solute in the mother liquor after separation from the first crop product. Also, the presence of the impurities requires special processing of the total crude TMLA to obtain it in commercially acceptable quality as its intramolecular anhydride.

The staged addition of bromine in combination with the addition of lead (IV) leads to higher yields of TMLA. This oxidation is conducted using acetic acid reaction medium in the weight ratio to PSC of about 0.5:1.0 to about 4.0:1.0. The metal oxidation catalyst components are lead (IV), cobalt, zirconium and manganese or cobalt and manganese. Total metal concentration excluding lead (IV) based on PSC is in the range of about 2.0 to about 20, preferably about 2.2 to about 15, milligram atoms in combination with a source of bromine providing a bromine concentration of about 1.5 to about 50.0, preferably about 1.6 to about 30.0, milligram atoms per mole PSC. The manganese component of the catalyst is at least 10 weight percent, preferably in the range of about 14.0 to about 50.0 weight percent based on the total weight of catalyst metals. The zirconium content of the total metals used in the range of about 1.0 to about 10, preferably about 1.5 to about 8.0, percent by weight of total metals. The cobalt component of the catalyst is in the range of about 50 to about 90 weight percent of the total metals. The lead (IV) component is about 1000 to about 8000 parts per million by weight based on the PSC feedstock.

When the oxidation of PSC is conducted batchwise, all of the PSC and most (90–99%) of the acetic acid and initial amount of catalyst components are charged at or near oxidation initiation temperature, preferably at about 120° C. to about 180° C., and at a pressure to maintain liquid phase conditions. Then, pressurized air is injected into the reaction mixture and the reaction temperature is permitted to increase by heat evolved by the oxidation reaction to about 175° C. to about 225° C.

The total bromine added can be from a single source of bromine, for example, ionic bromine sources (HBr, NaBr, NH$_4$BR and the like) or from a combined form of bromine, for example, organic bromides such as benzyl bromide, tetrabromoethane and others.

Our novel process relates to the liquid phase oxidation of PSC to TMLA using lead (IV), cobalt, manganese and/or other variable-valence metals plus bromine and, when desired, zirconium. A useful catalyst for our process is a zirconium-cobalt-manganese-bromine catalyst wherein the molecular ratio of zirconium to cobalt is about 1 to about 10 to about 1 to about 100 and the oxidation is conducted at a temperature in the range of about 120° C. to about 225° C., which process comprises conducting a batch oxidation of the PSC so that the first stage is a continuous or alternatively is a batch-stage oxidation of PSC so that the concentration of bromine in the first stage is 0 to about 0.5 mole per mole of metals while all the remaining bromine is added during the second stage. The total amount of bromine added is about 60 to about 180 weight percent of the total metal catalysts present. The reaction is completed in a batchwise process at a temperature of about 140° C. to about 250° C. and, if desired, the solvent and water of reaction are withdrawn during the last 5 to about 20% of the period of the reaction, usually during the last 5 to 20 minutes of the reaction, thus leaving a higher TMLA concentration in the liquid phase oxidation reactor effluent.

In an advantageous embodiment of our process for the oxidation of PSC with molecular oxygen to TMLA under liquid phase conditions in the presence of a zirconium-cobalt-manganese-bromine catalyst, the molecular ratio of zirconium to cobalt is about 1:10 to about 1:100 and the initial temperature is in the range of about 120° C. to about 180° C. This process comprises conducting a batch oxidation of the PSC so that in the first stage the amount of bromine added is below about 35 weight percent of the total bromine to be added. Also, this process comprises permitting only partial oxidation of the trimethylbenzene and thus avoiding the poisoning of the catalyst and completing the reaction in a batch process at a temperature of about 140° C. to about 175° C. to about 150° C. to about 250° C. During the last 5 to about 20 percent of the reaction time, the solvent and water of reaction are withdrawn leaving about 60 to about 75 weight percent solids in the crystallizer effluent.

The following examples illustrate the preferred embodiment of this invention. It will be understood that the examples are for illustrative purposes only and do not purport to be wholly definitive with respect to the conditions and scope of the invention.

In Table I, we have listed the results of several oxidations to which lead (IV) was added at various levels. The addition of lead (IV) in small amounts (0.20 to 0.60 wt % of PSC) provides a yield increase of about 0.2 to about 0.6 mole % by reducing high boilers. In addition, the color as measured by the $\Delta E$ colorimetry technique also improved with increasing lead levels. Lead may be acting as a selective poison as evidenced by the increasing run time as lead increases.

EXAMPLE 1

The oxidation of PSC was accomplished by bubbling air through a hot (320° F.) mixture of PSC (225 g) with 420 g of 95% acetic acid in the presence of cobalt and manganese acetates and HBr and zirconium to 320° F. The base case concentration of cobalt was 0.175 wt %, manganese was 0.084 wt %, Zr was 0.004 wt %, all based on PSC. Enough HBr was added to equal a 0.7 to 1.0 molar bromine to metals ratio but only 20% of the total bromine was added at the beginning of the oxidation. The remainder was added gradually with the so-called tailout catalyst which also included some manganese (0.01 wt %) and zirconium (0.005%).

The temperature was gradually ramped from 320° F. to 410° F. over the 60 minute run and pressure was also ramped from about 150 psig to about 400 psig over the same period. After the oxidation the reactor contents were collected and analyzed.

EXAMPLE 2

The same oxidation was performed but 1.0g of the lead (IV) acetate was added to the initial catalyst mixture.

EXAMPLE 3

The conditions and catalyst levels were identical to that of Example 1 but 1.75 g of lead (IV) acetate was added to the initial reaction mix.

EXAMPLE 4

The conditions and catalyst levels were identical to that of Example 1 but 2.5 g of lead (IV) acetate was added to the initial reaction mix.

The mole % yield breakdown for each of these runs is shown in Table I and indicates the yield increase and high boiler reduction when employing the novel process.

TABLE I

| | The Effect of Lead on Pseudocumene Oxidations | | | |
|---|---|---|---|---|
| Mole % Yield | Example 1 Base Case | Example 2 .20 wt % Pb | Example 3 .36 wt % Pb | Example 4 .51 wt % Pb |
| TMLA | 89.7 | 89.8 | 89.8 | 90.3 |
| Intermediates | 0.9 | 0.8 | 1.0 | 1.0 |
| Low Boilers | 2.8 | 2.8 | 2.7 | 2.6 |
| High Boilers | 1.5 | 1.3 | 1.2 | 0.7 |
| $CO + CO_2$ | 5.1 | 5.2 | 5.3 | 5.4 |
| $\Delta E^a$ | 48.9 | 45.4 | 33.8 | 30.1 |
| Run Time, min | 61 | 66 | 68 | 69 |

[a]This $\Delta E$ value is related to the color of the TMLA product in the 400–700 nm wavelength range as measured by a spectrophotometer. The lower the number, the lower the concentration of the undesirable colored impurities.

We claim:

1. In a process for oxidizing pseudocumene to trimellitic acid which comprises catalytically oxidizing the pseudocumene feedstock with air in an aliphatic acid solvent of about 2–5 carbon atoms, in an oxidation zone wherein liquid phase conditions are maintained, and wherein the weight ratio of the aliphatic acid solvent to the pseudocumene feedstock is in the range of about 0.5–40:1.0 and the catalyst comprises cobalt, manganese and bromine components, the improvement comprises employing a combination of sources of cobalt, manganese, and bromine componenets so as to provide about 0.05 to about 0.4 weight percent total of cobalt and manganese combined, based on the pseudocumene feedstock and such that the weight ratio of bromine ions to total metals ions is about 0.5–3.0:1.0, and the manganese content is about 10–50 percent, each by weight of the total metals; adding about 1000–8000 parts per million by weight of lead (IV) based on the weight of the pseudocumene and in one or two stages; and conducting the reaction at a temperature of about 100° C. to about 275° C.

2. The process of claim 1 wherein the aliphatic acid is acetic acid.

3. The process of claim 1 wherein the addition of bromine is conducted in two stages and more than half of the bromine is added in the second stage.

4. The process of claim 1 wherein about 3000 to about 6000 parts per million by weight of lead (IV) based on the pseudocumene feedstock are added.

5. The process of claim 1 wherein the catalyst additionally comprises a zirconium component at a level of 1-10 weight percent of the total metal content of the catalyst.

6. The process of claim 1 wherein the pseudocumene feedstock is catalytically oxidized with oxygen.

* * * * *

UNITED STATES PATENT OFFICE
CERTIFICATE OF CORRECTION

Patent No. 4,845,275  Dated July 4, 1989

Inventor(s) Wayne P. Schammel & Michael R. Green

It is certified that error appears in the above-identified patent and that said Letters Patent is hereby corrected as shown below:

Column 1, Line 15, "varia- ble-valence" should be --variable valence--

Column 6, Line 58, "componenets" should be --components--

Signed and Sealed this

Thirtieth Day of April, 1991

Attest:

HARRY F. MANBECK, JR.

Attesting Officer  Commissioner of Patents and Trademarks